(12) United States Patent
Sommer et al.

(10) Patent No.: US 10,080,628 B2
(45) Date of Patent: *Sep. 25, 2018

(54) SELF-LIGATING BRACKET

(71) Applicant: American Orthodontics Corporation, Sheboygan, WI (US)

(72) Inventors: Jay S. Sommer, Howards Grove, WI (US); Eric W. Nimmer, Plymouth, WI (US); Andrew R. Pietzner, Sheyboygan, WI (US)

(73) Assignee: American Orthodontics Corporation, Sheboygan, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/176,777

(22) Filed: Jun. 8, 2016

(65) Prior Publication Data

US 2016/0354181 A1 Dec. 8, 2016

Related U.S. Application Data

(60) Provisional application No. 62/172,548, filed on Jun. 8, 2015.

(51) Int. Cl.
*A61C 7/28* (2006.01)
(52) U.S. Cl.
CPC .................... *A61C 7/287* (2013.01)
(58) Field of Classification Search
CPC ............. A61C 7/30; A61C 7/25; A61C 7/143
USPC ......................................................... 433/11
See application file for complete search history.

(56) References Cited

U.S. PATENT DOCUMENTS

| | | |
|---|---|---|
| 2,549,528 A | 4/1951 | Russell |
| 2,671,964 A | 3/1954 | Russel et al. |
| 3,131,474 A | 5/1964 | Johnson |
| 4,197,642 A | 4/1980 | Wallshein |
| 4,248,588 A | 2/1981 | Hanson |
| 4,419,078 A | 12/1983 | Pletcher |
| 4,492,573 A | 1/1985 | Hanson |
| 5,094,614 A | 3/1992 | Wildman |
| 5,275,557 A | 1/1994 | Damon |
| 5,322,435 A | 6/1994 | Pletcher |

(Continued)

FOREIGN PATENT DOCUMENTS

| | | |
|---|---|---|
| DE | 1407100 | 9/1995 |
| DE | 102009029834 A1 | 12/2010 |

(Continued)

OTHER PUBLICATIONS

International Search Report and Written Opinion of PCT International Application No. PCTUS2016/036452, dated Sep. 7, 2016.

(Continued)

*Primary Examiner* — Nicholas Lucchesi
*Assistant Examiner* — Shannel Wright
(74) *Attorney, Agent, or Firm* — Andrus Intellectual Property Law, LLP

(57) ABSTRACT

A self-ligating bracket includes a bracket body and a spring clip. The bracket body includes a mesial channel, a distal channel, a center channel, and an arch wire slot. The spring clip includes a distal arm, mesial arm, and a center arm which are moveably within the mesial channel, distal channel, and center channel between an open position and a closed position to occlude the arch wire slot.

12 Claims, 6 Drawing Sheets

(56) References Cited

U.S. PATENT DOCUMENTS

| | | |
|---|---|---|
| 5,429,500 A | 7/1995 | Damon |
| 5,439,378 A * | 8/1995 | Damon .................. A61C 7/146 |
| | | 433/13 |
| 5,466,151 A | 11/1995 | Damon |
| 5,474,445 A | 12/1995 | Voudouris |
| 5,474,446 A | 12/1995 | Wildman et al. |
| 5,562,444 A * | 10/1996 | Heiser ..................... A61C 7/30 |
| | | 433/11 |
| 5,613,850 A | 3/1997 | Wildman et al. |
| 5,630,715 A | 5/1997 | Voudouris |
| 5,711,666 A | 1/1998 | Hanson |
| 5,800,162 A | 9/1998 | Shimodaria et al. |
| 5,857,849 A | 1/1999 | Kurz |
| 5,857,850 A | 1/1999 | Voudouris |
| 5,906,486 A | 5/1999 | Hanson |
| 5,908,293 A * | 6/1999 | Voudouris ................ A61C 7/02 |
| | | 433/10 |
| 5,913,680 A | 6/1999 | Voudouris |
| 6,071,118 A | 6/2000 | Damon |
| 6,071,119 A | 6/2000 | Christoff |
| 6,168,428 B1 | 1/2001 | Voudouris |
| 6,247,923 B1 | 6/2001 | Vashi |
| 6,257,883 B1 * | 7/2001 | Voudouris ................ A61C 7/02 |
| | | 433/11 |
| 6,325,622 B1 | 12/2001 | Kelly et al. |
| 6,368,105 B1 | 4/2002 | Voudouris et al. |
| 6,464,495 B1 | 10/2002 | Voudouris |
| 6,554,612 B2 | 4/2003 | Georgakis et al. |
| 6,632,088 B2 | 10/2003 | Voudouris |
| 6,659,766 B2 | 12/2003 | Abels et al. |
| 6,733,286 B2 * | 5/2004 | Abels ..................... A61C 7/125 |
| | | 433/11 |
| 6,776,613 B2 | 8/2004 | Orikasa |
| 6,843,651 B2 * | 1/2005 | Orikasa .................. A61C 7/287 |
| | | 433/13 |
| 6,939,133 B2 | 9/2005 | Voudouris |
| 7,104,791 B2 | 9/2006 | Hanson |
| 7,214,057 B2 | 5/2007 | Voudouris |
| 7,247,019 B2 | 7/2007 | Abels et al. |
| 7,255,557 B2 | 8/2007 | Forster |
| 7,267,545 B2 | 9/2007 | Oda |
| 7,335,020 B2 * | 2/2008 | Castner .................. A61C 7/287 |
| | | 433/11 |
| 7,416,408 B2 | 8/2008 | Farzin-Nia et al. |
| 7,419,375 B2 | 9/2008 | Farzin-Nia et al. |
| 74,442,039 | 10/2008 | Opin |
| 7,481,651 B2 | 1/2009 | Sernetz et al. |
| 7,611,353 B2 | 11/2009 | Sommer |
| 7,621,743 B2 * | 11/2009 | Bathen ................... A61C 7/287 |
| | | 433/10 |
| 7,704,072 B2 * | 4/2010 | Damon ................... A61C 7/287 |
| | | 433/11 |
| 7,785,101 B2 | 8/2010 | Forster |
| 7,845,939 B2 | 12/2010 | Minium |
| 7,909,603 B2 * | 3/2011 | Oda ........................ A61C 7/287 |
| | | 433/10 |
| 7,963,767 B2 | 6/2011 | Lewis et al. |
| 8,029,276 B1 * | 10/2011 | Lokar ..................... A61C 7/287 |
| | | 433/10 |
| 8,033,824 B2 | 10/2011 | Oda et al. |
| 8,038,438 B2 * | 10/2011 | Ruiz Diaz ................ A61C 7/14 |
| | | 433/11 |
| 8,113,827 B2 | 2/2012 | Farzin-Nia et al. |
| 8,246,348 B2 * | 8/2012 | Heiser ..................... A61C 7/14 |
| | | 433/10 |
| 8,246,349 B2 | 8/2012 | Scommegna et al. |
| 8,251,696 B2 * | 8/2012 | Rodriguez .............. A61C 7/287 |
| | | 433/10 |
| 8,282,392 B2 * | 10/2012 | Hilliard ................... A61C 7/22 |
| | | 433/11 |
| 8,297,970 B2 * | 10/2012 | Kanomi ................... A61C 7/14 |
| | | 433/11 |
| 8,393,896 B2 | 3/2013 | Oda |
| 8,414,292 B2 | 4/2013 | Lopes |
| 8,568,138 B2 * | 10/2013 | Farzin-Nia ............. A61C 7/287 |
| | | 433/10 |
| 8,585,398 B2 * | 11/2013 | Yeh ........................ A61C 7/287 |
| | | 433/10 |
| 8,636,507 B2 | 1/2014 | Voudouris |
| 8,726,510 B2 | 5/2014 | Voudouris |
| D710,998 S | 8/2014 | Voudouris |
| 8,932,053 B2 | 1/2015 | Curiel et al. |
| 8,944,811 B2 | 2/2015 | Curiel et al. |
| 2002/0187452 A1 * | 12/2002 | Abels ..................... A61C 7/143 |
| | | 433/11 |
| 2003/0039938 A1 | 2/2003 | Orikasa |
| 2004/0166459 A1 | 8/2004 | Voudouris |
| 2004/0170942 A1 * | 9/2004 | Heiser ..................... A61C 7/28 |
| | | 433/11 |
| 2004/0175667 A1 | 9/2004 | Abels et al. |
| 2004/0175669 A1 | 9/2004 | Abels et al. |
| 2004/0175699 A1 | 9/2004 | Fiszman |
| 2005/0239012 A1 * | 10/2005 | Bathen ................... A61C 7/287 |
| | | 433/10 |
| 2005/0244772 A1 * | 11/2005 | Abels ..................... A61C 7/285 |
| | | 433/8 |
| 2007/0072143 A1 * | 3/2007 | Sommer ................. A61C 7/285 |
| | | 433/10 |
| 2007/0166658 A1 | 7/2007 | Voudouris |
| 2007/0178422 A1 * | 8/2007 | Voudouris ............... A61C 7/287 |
| | | 433/10 |
| 2009/0004617 A1 | 1/2009 | Oda et al. |
| 2009/0325119 A1 | 12/2009 | Sierk |
| 2010/0105000 A1 * | 4/2010 | Scommegna .......... A61C 7/287 |
| | | 433/10 |
| 2010/0261131 A1 | 10/2010 | Ruiz-Vela et al. |
| 2010/0311004 A1 * | 12/2010 | Voudouris ............... A61C 7/287 |
| | | 433/11 |
| 2011/0076633 A1 * | 3/2011 | Bryant .................... A61C 7/287 |
| | | 433/11 |
| 2011/0136071 A1 * | 6/2011 | Levens ................... A61C 7/125 |
| | | 433/13 |
| 2012/0028206 A1 * | 2/2012 | Lopes ..................... A61C 7/287 |
| | | 433/10 |
| 2013/0125398 A1 | 5/2013 | Curiel et al. |
| 2013/0171579 A1 | 7/2013 | Orikasa et al. |
| 2013/0196279 A1 | 8/2013 | Curiel et al. |
| 2013/0260329 A1 | 10/2013 | Voudouris |
| 2013/0337397 A1 | 12/2013 | Curiel et al. |
| 2013/0337399 A1 | 12/2013 | Curiel et al. |
| 2014/0011154 A1 | 1/2014 | Curiel et al. |
| 2014/0023981 A1 | 1/2014 | Voudouris |
| 2014/0134563 A1 | 5/2014 | Voudouris |
| 2014/0199648 A1 | 7/2014 | Lopes |
| 2014/0212828 A1 * | 7/2014 | Falcone .................. A61C 7/14 |
| | | 433/11 |
| 2014/0272750 A1 * | 9/2014 | Lai ......................... A61C 7/287 |
| | | 433/9 |
| 2014/0272753 A1 * | 9/2014 | Sommer ................. A61C 7/30 |
| | | 433/11 |
| 2014/0308622 A1 * | 10/2014 | Voudouris ............... A61C 7/14 |
| | | 433/10 |
| 2015/0125804 A1 * | 5/2015 | D'Amico Neto ...... A61C 7/287 |
| | | 433/10 |
| 2015/0216629 A1 * | 8/2015 | Voudouris ............... A61C 7/30 |
| | | 433/9 |
| 2015/0265377 A1 * | 9/2015 | Wu ........................ A61C 7/287 |
| | | 433/11 |

FOREIGN PATENT DOCUMENTS

| | | |
|---|---|---|
| EP | 161831 | 3/1996 |
| EP | 1234549 | 8/2002 |
| EP | 1287789 | 3/2003 |
| EP | 2644150 A1 | 10/2013 |
| FR | 2922753 | 12/2010 |
| WO | 1998020805 | 5/1998 |
| WO | 2008044912 | 4/2008 |

(56) References Cited

FOREIGN PATENT DOCUMENTS

| WO | 2010028276 | 3/2010 |
|----|------------|--------|
| WO | 2010103178 | 9/2010 |
| WO | 2006094403 | 9/2016 |

OTHER PUBLICATIONS

Agility Self-Ligating Passive System by Orthodontic Design and Production, Inc., acquired Mar. 10, 2014.
Easy Clip, Self-Ligating Bracket Systems Brochure by Great Lakes Orthodontics, LTD, Oct. 2015.

* cited by examiner

SELF-LIGATING BRACKET

CROSS-REFERENCE TO RELATED APPLICATION

The present application claims priority of U.S. Provisional Patent Application No. 62/172,548, filed on Jun. 8, 2015, the content of which is hereby incorporated herein by reference in its entirety.

BACKGROUND

The present disclosure relates to the field of orthodontics. More specifically, the present disclosure relates to self-ligating brackets.

Orthodontic treatment often involves at least a combination of an arch wire and brackets and/or buccal tubes that are used to secure the arch wire to the teeth of the patient. The arch wire is made of a resilient material that, if bent or deformed, will return to its previous shape. Dental malocclusions are treated by securing the arch wire to the patient teeth which are brought into a post-treatment alignment as the arch wire returns to its original shape. The corrective forces are transferred from the interactions between the arch wire and the arch wire slot of the bracket, through the bracket to the tooth.

Traditionally, brackets are secured to the teeth of a patient and the brackets have an arch wire slot within which the arch wire is received. Elastomeric ligatures secure the arch wire within the arch wire slot of the bracket. Self-ligating brackets include a built in mechanical ligature which eliminates the need for separate elastomeric ligatures to secure the arch wire to the bracket. Self-ligating brackets typically use a sliding and/or rotating clip or door that moves relative to the bracket body to occlude the arch wire slot.

Self-ligating brackets are available as "active" brackets or "passive" brackets, which describe the way in which the arch wire may interact with the clip. Active self-ligating brackets include a clip in which an end or portion extends into an edgewise slot and resiliently applies a seating force against an arch wire in the facial-lingual dimension. The active self-ligating bracket retains the arch wire in the slot due to the mechanical strength of the clip itself. Active self-ligating brackets provide more control of the interactive forces between the clip and the arch wire, but can increase friction between the arch wire and the clip, which may reduce the transfer of this force to the tooth.

Passive self-ligating brackets include a clip that extends across and beyond the arch wire slot and is fixed or restrained against movement in the facial-lingual dimension. The passive self-ligating bracket, when closed, effectively forms a tube defined by the slot and the clip within which an arch wire with a diameter smaller than a diameter of the formed tube can slide. For this reason, in some applications, the clip of a passive self-ligating bracket is called a door.

BRIEF DISCLOSURE

An exemplary embodiment of a self-ligating bracket includes a bracket body. The bracket body includes a mesial side and a distal side. The bracket body includes an arch wire slot that extends from the mesial side to the distal side of the bracket body. A mesial channel extends into the bracket body. A center channel extends into the bracket body between the mesial channel and the distal channel. A spring clip includes a distal arm which includes a distal arm body and a distal finger. The spring clip includes a mesial arm which includes a mesial arm body and a mesial finger. The spring clip includes a center arm which includes a first center arm body and a second arm center body. The first center arm body and the second arm body are connected by a center arm bar. The spring clip is movable between an open position and a closed position. In the open position, the arch wire slot is unobstructed and in the closed position the distal finger, the mesial finger, and the center arm bar extend into and across the arch wire slot to occlude the arch wire slot.

DETAILED DISCLOSURE

Figure 1A:
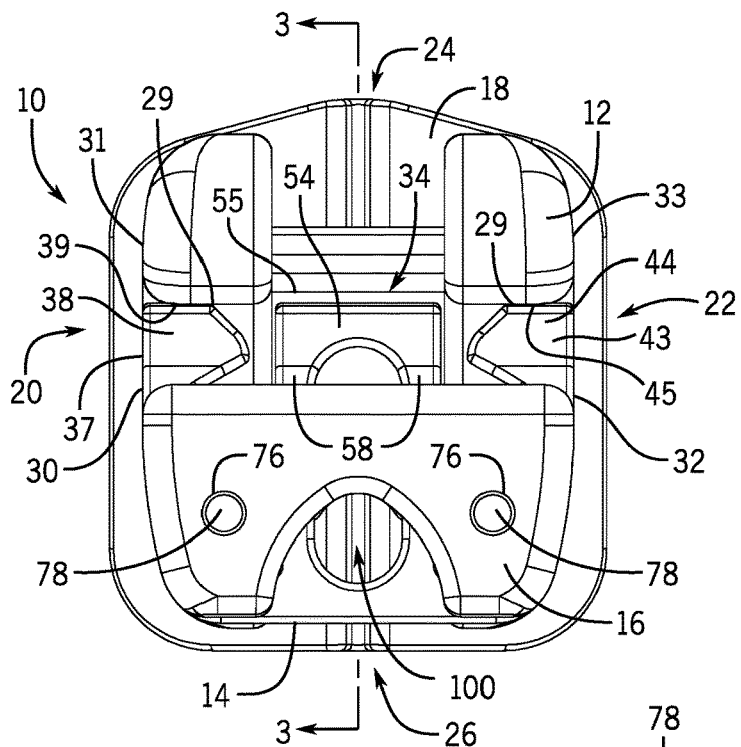
FIG. 1A is a top view of an exemplary embodiment of a self-ligating bracket in a closed configuration.

FIGS. 1-6 all depict various views of a first exemplary embodiment of a self-ligating bracket 10. The self-ligating bracket 10 generally includes a bracket body 12, a spring clip 14, and a bracket cap 16. In embodiments, a bonding pad 18 is secured to the bracket body 12. The bonding pad 18 may be exemplarily secured to the bracket body 12 by braising or welding. In alternative embodiments, the bonding pad 18 may be secured to the bracket body 12 by being integral to one another and being exemplarily formed by casting or milling, although it will be understood that alternative techniques of manufacturing the bracket body 12 and bonding pad 18 may be used. In embodiments, the bonding pad 18 may be formed or contoured such as to be secured to a tooth of a patient's dentition. Applicant's co-pending U.S. patent application Ser. No. 14/212,616 filed on Mar. 14, 2014 further described aspects of self-ligating brackets and is hereby incorporated by reference in its entirety.

The self-ligating bracket 10 exemplarily includes a distal side 20, a mesial side 22, a gingival side 24, and an occlusal side 26. It will be recognized that these designations are relative and informational and alternative embodiments may be positioned in other orientations within the mouth of the patient while remaining within the scope of the embodiments as disclosed herein.

Figure 1B:
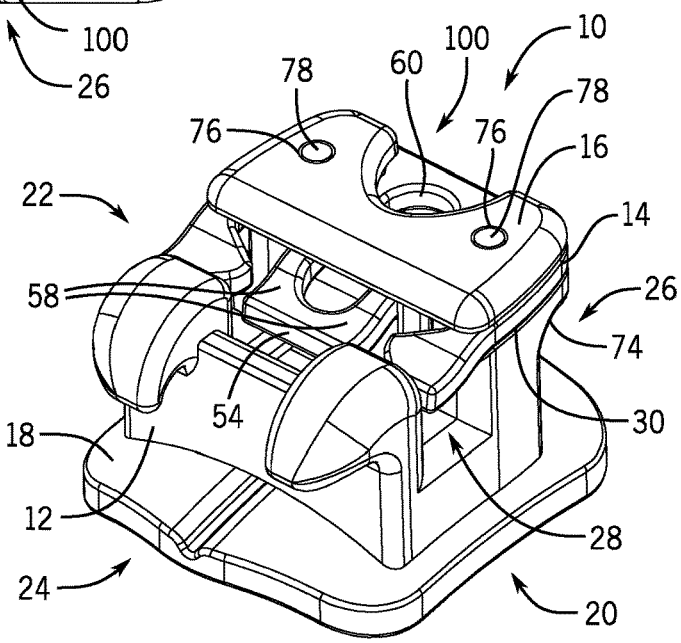
FIG. 1B is a perspective view of an exemplary embodiment of a self-ligating bracket in a closed configuration.
Figure 1C:
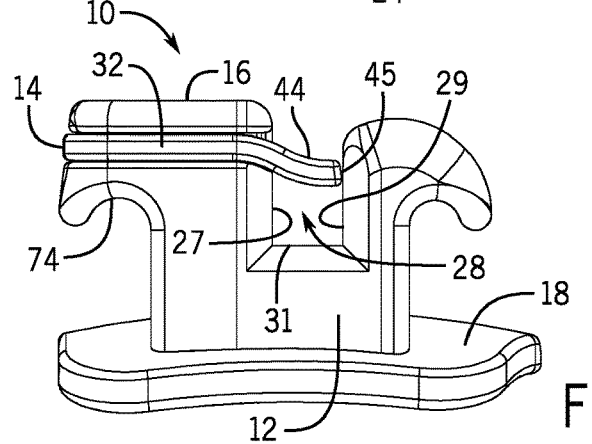
FIG. 1C is a side view of an exemplary embodiment of a self-ligating bracket in a closed configuration.
Figure 2A:
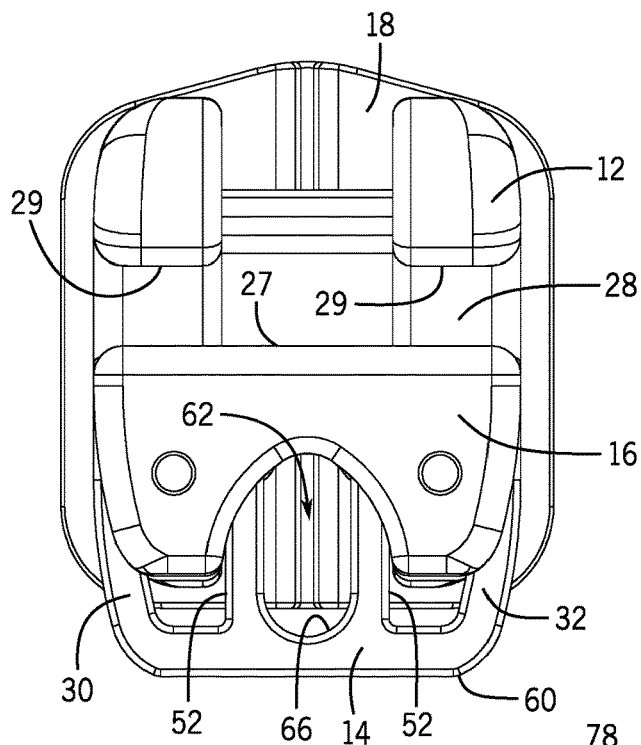
FIG. 2A is a top view of an exemplary embodiment of a self-ligating bracket in an open configuration.
Figure 2B:
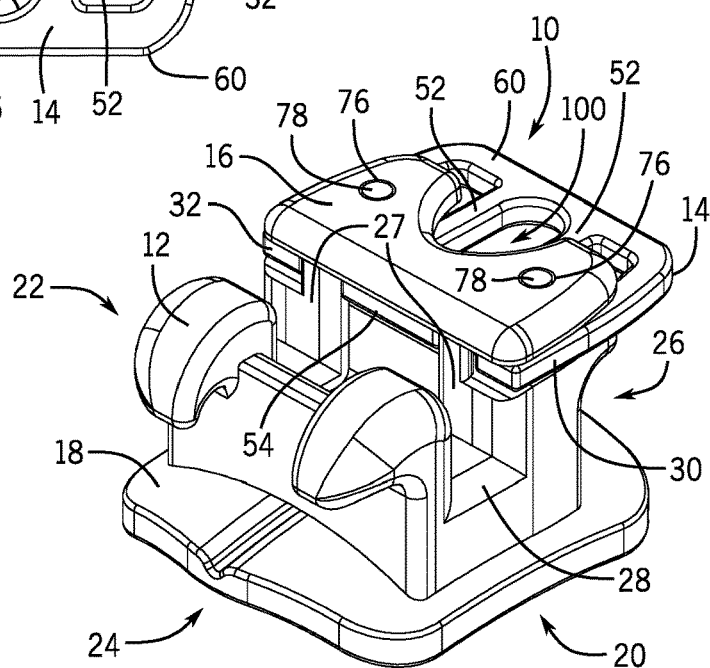
FIG. 2B is a perspective view of an exemplary embodiment of a self-ligating bracket in an open configuration.
Figure 2C:
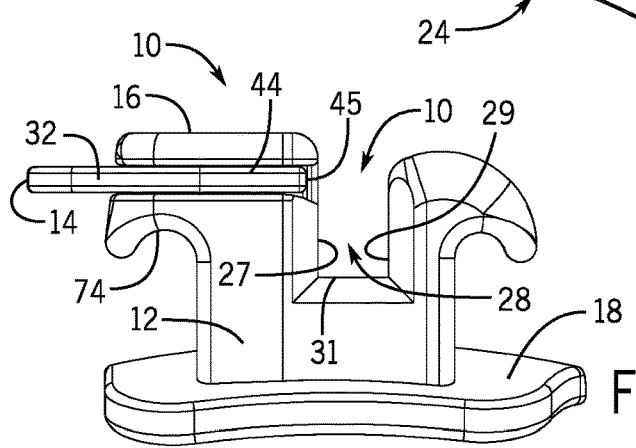
FIG. 2C is a side view of an exemplary embodiment of a self-ligating bracket in an open configuration.

FIGS. 1A-C depict various views of the first exemplary embodiment of the self-ligating bracket 10 in a closed configuration in which the spring clip 14 is moved to a closed position that occludes an arch wire slot 28. FIGS. 2A-C depict various views of the first exemplary embodiment of the self-ligating bracket 10 in an open configuration in which the spring clip 14 is moved to a position in which the arch wire slot 28 is accessible to receive an arch wire (not depicted). When the self-ligating bracket 10 is in the open configuration, the spring clip 14 is in the open position away from the arch wire slot 28 and the arch wire slot 28 is able to receive an arch wire. When the self-ligating bracket 10 is in the closed configuration, the spring clip 14 is in a closed position extending across and into the arch wire slot 28 in a manner that operates to retain the arch wire during use to orthodontically treat the dentition of a patient. Specific features and interaction within the embodiment will be described in further detail herein with respect to FIGS. 4-6.

Figure 4A:
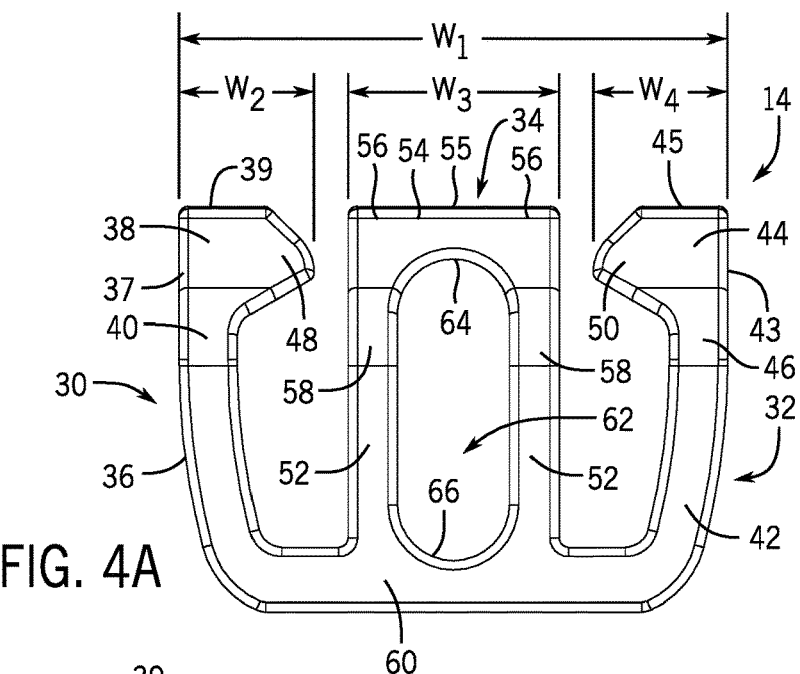
FIG. 4A is a top view of an exemplary embodiment of a spring clip.
Figure 4B:
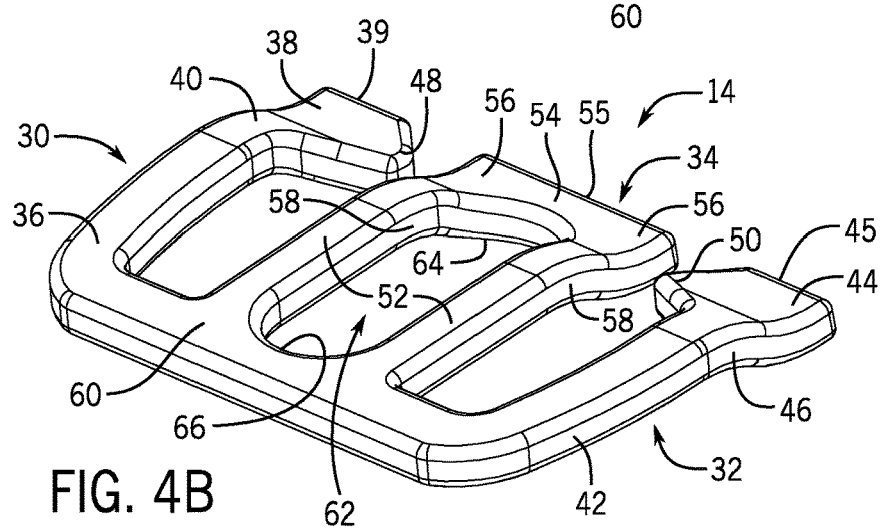
FIG. 4B is a perspective view of an exemplary embodiment of a spring clip.

FIG. 4A is a top view of a spring clip 14. FIG. 4B is a perspective view of the spring clip 14. The spring clip 14 includes a distal arm 30, a mesial arm 32, and a center arm 34. The distal arm 30 further includes a distal arm body 36 and a distal finger 38. The distal arm 30 terminates in a distal arm end 39. The distal finger 38 is connected to the distal arm body 36 by a distal transition portion 40. In an exemplary embodiment, the distal transition portion 40 is formed as an S-curve between the distal arm body 36 and the distal finger 38, although it will be recognized that the distal transition portion 40 may take a variety of other shapes or forms while staying within the scope of the present disclosure. In embodiments, at least a portion of the distal finger 38 is planar and extends in a different plane than the distal arm body 36. In some embodiments, the distal finger 38 may extend parallel to the distal arm body 36. In other embodiments, the distal finger 38 may extend at another angle or curvature. The mesial arm 32 similarly includes a mesial arm body 42 connected to a mesial finger 44 by a mesial transition portion 46. The mesial arm 32 terminates in a mesial arm end 45. In an embodiment, the mesial arm 32 is constructed in similar manners as described above with respect to the distal arm 30.

In still further embodiments as described herein, the distal arm 30 includes a distal projection 48. In an embodiment, the distal projection 48 extends interior to the self-ligating bracket 14 from the distal finger 38. Similarly, the mesial arm 32 further includes a mesial projection 50 that extends into the self-ligating bracket 14 exemplarily from the mesial finger 44.

The center arm 34 is exemplarily constructed of two generally opposed center arm bars 52 connected by an end bar 54. The center arm 34 terminates in a center arm end 55. The end bar 54 exemplarily extends across and connects gingival ends 56 of the respective center arm bars 52. The end bar 54 exemplarily extends in the same plane as the distal finger 38 and mesial finger 44. In still further exemplary embodiments, the end bar 54 extends in the same plane as the distal projection 48 and the mesial projection 50. The center arm bars 52 exemplarily further include center transition portions 58, which are exemplarily S-curves. In exemplary embodiments, similar components respectively between the distal arm 30, mesial arm 32 and center arm 34 extend in a same plane when viewed looking mesially-distally, as like components across these structures. The spring clip 14 further includes a base bar 60 that may generally extend along a length of the spring clip 14 in the mesial-distal dimension. The distal arm 30, mesial arm 32, and center arm 34 all exemplarily extend away from the base bar 60.

As best depicted by way of reference to FIGS. 1A and 4A, a total width $W_1$ of the spring clip 14 between the distal arm 30 and the mesial arm 32 exemplarily coincides with the bracket body 12 in total width in the mesial-distal dimension. More specifically, a distal edge 37 of the distal arm 30, and particularly the distal finger 38 is aligned with a distal side 31 of the bracket body 12 and a mesial edge of the mesial arm 32, and particularly the mesial finger 44 is aligned with a mesial side 33 of the bracket body 12. Thus, when the spring clip 14 is in the closed position, the distal arm 30 and mesial arm 32 apply their restraining forces on an arch wire starting at the respective distal and mesial ends of the arch wire slot 28. Additionally, the center arm 34, more specifically, the center arm bar 54 provides the restraining force on an arch wire at the center of the arch wire slot 28, and similarly the center of the bracket 12.

The distal finger 38 has a width $W_2$, the center bar 54 has a width $W_3$, and the mesial finger 44 has a width $W_4$. These widths represent the portion of the spring clip 14 that are configured to engage an arch wire in the slot 28. Thus a combined width ($W_2+W_3+W_4$), while necessarily less than or equal to $W_1$, represents the amount of the arch wire slot 28 that is occluded when the clip 14 is in the closed position. In an embodiment, the combined width is 60% or more of $W_1$. In still further embodiments, the distal projection 48 increases $W_2$ beyond the width of the distal arm body 36 and the mesial projection 50 increases $W_4$ beyond the width of the mesial arm body 42 and the combined width is a greater percentage of $W_1$. In one exemplary embodiment the distal and mesial projections are at least twice as wide as the respective widths of the distal arm body 36 and the mesial arm body 42 and the combined width is 80% or more of $W_1$. In a still further exemplary embodiment, for example as depicted in FIGS. 1-6, the combined width is 85% or more of $W_1$. In a still further embodiment, by enlargement of one or more of the center bar 54, distal finger 38, and mesial finger 44 the combined width is 90% or more of $W_1$. It will be understood that these embodiments are merely exemplary and additional configurations of components making up $W_2$, $W_3$, and $W_4$ will be recognized while being within the scope of the present disclosure. Therefore, embodiments exhibit the advantage of separate engagement forces, applied at the distal, mesial, and center of the bracket across a great portion of the arch wire slot.

The center arm bars 52 and end bar 54 exemplarily define a center opening 62. The center opening 62 exemplarily includes a first end 64, which may be generally flat as defined by the end bar 54 and a second end 66 that may be rounded in shape and defined by a curve formed into the center arm bars 52 and base bar 60. It will be recognized that the center opening 62 may exemplarily take other shapes while still remaining within the scope of the present disclosure.

Figure 5:
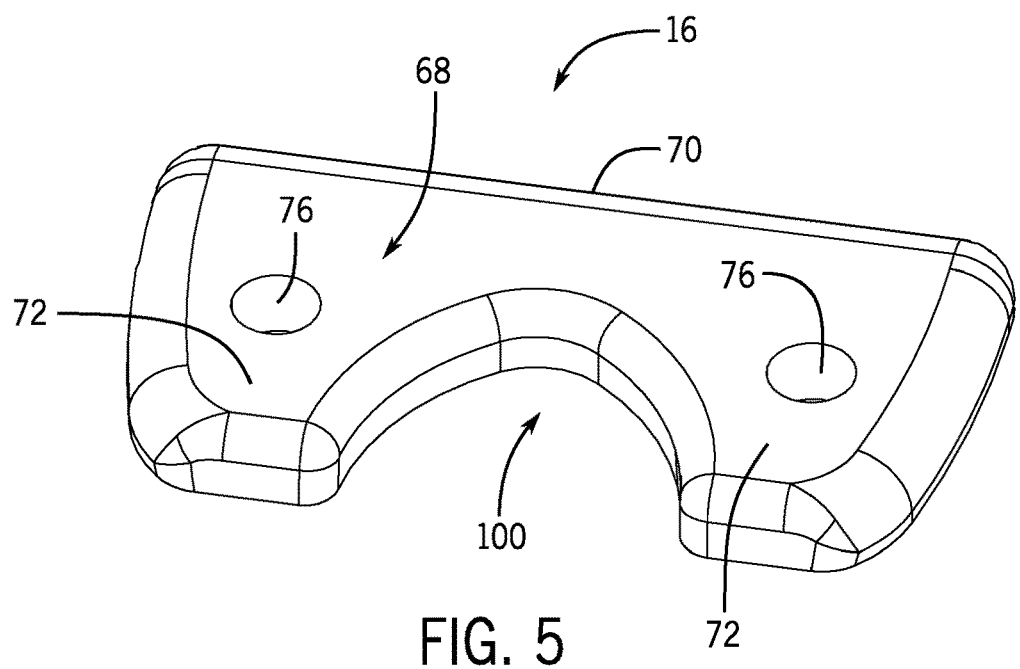
FIG. 5 is a perspective view of an exemplary embodiment of a bracket cap.

FIG. 5 is a perspective view of an exemplary embodiment of a bracket cap 16 as will be described in further detail herein. The bracket cap 16 has a generally planar top surface

Figure 3:
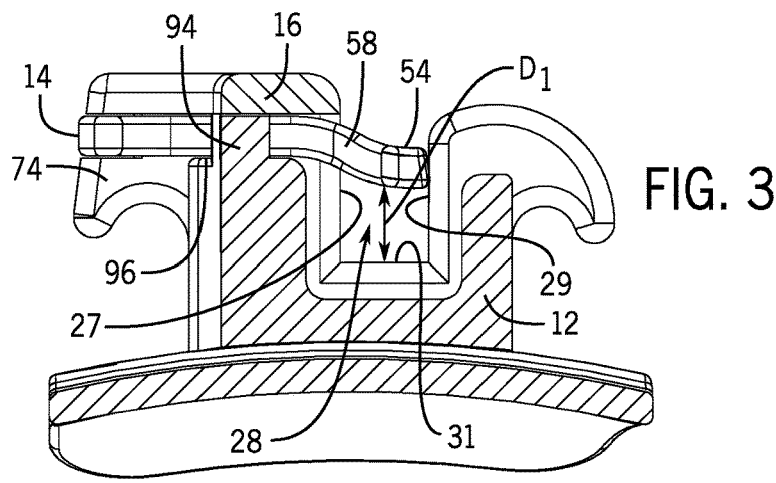
FIG. 3 is a side sectional view of the self-ligating bracket taken along line 3-3 of FIG. 1A.

68. At an exemplary gingival side, the bracket cap 16 includes an arch wire slot side 70. Opposite the arch wire slot side 70, the bracket cap ends in two tie wing caps 72. The bracket cap 16 is configured to matingly engage the bracket body 12 in the manners as depicted in FIGS. 1-3. In such engagement, the arch wire slot side 70 is aligned with an occlusal wall 27 of the arch wire slot 28 in the bracket body 12 and each of the tie wing caps 72 align with respective tie wings 74 of the bracket body 12.

The bracket cap 16 further includes post holes 76 that extend through the bracket caps 16 and are configured to engage posts 78 on the bracket body 12 as described in further detail herein.

Figure 6:
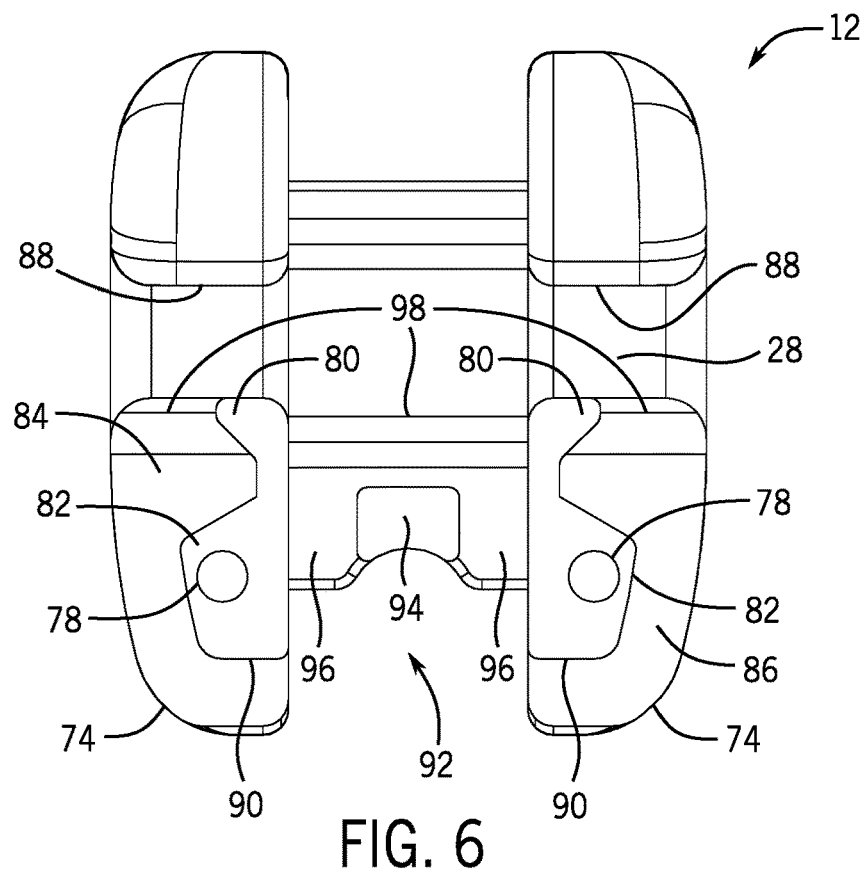
FIG. 6 is a top view of an exemplary embodiment of a bracket body.

FIG. 6 depicts various views of an exemplary embodiment of a bracket body 12. The bracket body 12 further includes a plurality of stop projections, exemplarily gingival stop projections 80 and occlusal stop projections 82 that respectively extend into a distal channel 84 within which the distal arm (not depicted) of the spring clip slides and the mesial channel 86 within which the mesial arm (not depicted) of the spring clip slides. The stop projections 80, 82 resiliently engage the distal projection 48 and the mesial projection 50 of the spring clip 14 (FIG. 4). In addition to other features as described in further detail herein, the engagement of the spring clip distal projection and mesial projection with the stop projection 80 and 82 of the bracket body 12 defines and open position of the spring clip. On the other hand, engagement of the distal finger 38 and mesial finger 44 with respective gingival sides 88 of the arch wire slot 28 as well as engagement of the base bar 60 with occlusal end 90 of the occlusal stop projections 82 define the closed position of the spring clip.

The bracket body 12 further includes a center channel 92 within which the center arm 34 of the spring clip slides, as depicted in FIGS. 1-3. A stop projection 94 is located within the center channel 92 and exemplarily extends upwards from a center channel floor 96 which is the surface that the center arm 34 of the spring clip slidingly engages. The stop projection 94 is exemplarily dimensioned such that it is can be slidingly received within the center opening 62 of the spring clip. When the center opening 62 of the spring clip 14 is arranged over the stop projection 94, the center arm 34 is slidably received within the center channel 92. The stop projection 94 extends through the center opening 62 where when the spring clip 14 is in the open position, the stop projection 94 engages the first end 64 of the center opening 62, which may be embodied by the end bar 54 of the center arm 34. Thus, the engagement of the stop projection 94 with the end bar 54 further defines the open position of the spring clip and prevents complete removal of the spring clip beyond the defined open position.

The bracket body 12 further includes shoulders 98 on the occlusal wall 27 of the arch wire slot 28 which effectively transition each of the distal channel 84, mesial channel 86, and center channel 92 into the ach wire slot 28. In embodiments, the respective transition portions 40, 46, and 58 of the distal arm 30, mesial arm 32, and center arm 34 are exemplarily shaped as S-curves which, due to the resilient material from which the spring clip is constructed, generally flatten as the spring clip is moved into the open position and withdrawn into the respective distal channel 84, mesial channel 86, or center channel 92. It will be further recognized that the distal channel 84, mesial channel 86, and center channel 92 are further defined on the labial side by the bracket cap 16 secured to the bracket body. As the spring clip is moved into the closed position, the S-curves of the transition portions return to their normal configuration and create a biasing force against the shoulders to retain the spring clip in the closed position.

Additionally, in exemplary embodiments, at least some of the arms are further reinforced against the arch wire escaping the arch wire slot when the clip is in the closed position. This may achieve improved ligating strength and robustness of embodiments of the bracket. In the exemplary embodiment depicted in FIGS. 1-6, the cap 16 provides a resilient force against each of the arms 30, 32, 34 in the facial-lingual dimension. This creates a short moment arm about which any force in the facial-lingual dimension from the arch wire against any arms 30, 32, 34 is resisted. The short moment arm increases the strength of the arms to resist this force. Additionally, in some embodiments, the arch wire slot side 70 of the cap16 may be in alignment with the occlusal wall 27 of the arch wire slot 28 which further minimizes this moment arm. A similar configuration and embodiment with similar advantages may be implemented in the embodiment of the bracket shown and described with respect to FIGS. 7-11, although in such embodiment, the caps 114 engage the mesial arm 30 and distal arm 32.

The bracket cap 16 further includes a tool cut out 100 that extends between the tie wing cap 72. The tool cut out 100 may exemplarily be defined as a complex curve defined by three curved sections comprising at least two radii. When the spring clip is in the closed position, the second end 66 of the center opening 62 of the spring clip 14 is aligned with the tool cut out 100 to facilitate access by an orthodontist's tool tip (not depicted) with the second end 66 of the center opening 62 such that the orthodontist can apply an opening force with the orthodontic tool tip to overcome the exemplary biasing forces, of the transition portion of the spring clip arms against the shoulders of the bracket body as well as the distal and mesial projections against the respective gingival stop projections of the base, to move the spring clip into the open position.

In an exemplary embodiment, the orthodontic tool creates a lever between the bracket body and the spring clip to move the spring clip from the closed position to the open position. The tool tip extends through the center opening and engages the bracket body through the center opening 62. The orthodontist uses a twisting or rotating movement to place a force in the gingival direction against the bracket body and a force in the occlusal direction against the spring clip. These forces overcome the biasing forces of the spring clip in the closed position to move the spring clip into the open position. However, this may provide improved patient comfort as the forces from the tool generally oppose one another creating less force felt by the patient in contrast to an embodiment wherein the tool tip only engages the spring clip with the force in the occlusal direction.

The above described structural features of the first embodiment of the self-ligating bracket 10 achieve the desirable feature of providing a self-ligating bracket 10 which includes a spring clip 14 that is captured between the bracket body 12 and the bracket cap 16. In assembly, the spring clip 14 is positioned on the bracket body 12, exemplarily in the closed position with the distal, mesial, and center arms positioned respectively in the distal, mesial, and center channels. The bracket cap 16 is secured to the bracket body 12, securing the spring clip 14 moveably between the bracket body 12 and the bracket cap 16. When the post holes 76 of the bracket cap engage the posts 78 of the bracket body, the bracket cap 16 can be secured, exemplarily by welding or braising to the bracket body 12. This is depicted in FIG. 3 which shows the bracket cap 16 secured to the bracket body 12 and in contact with the top of the stop projection 94. As can also be seen in FIG. 3, the distal channel, center channel, (and mesial channel) are exemplarily the same height as the thickness of the spring clip 14 such that the spring clip is slidable within the respective channels. Once secured, the bracket cap 16 traps the spring clip 14 in slidable engagement between the bracket cap 16 and bracket body 12. The spring clip 14 cannot be removed from the joined bracket body 12 and the bracket cap 16 because of the engagement of the end bar 54 with the stop projection 94 when the spring clip 14 is moved into the open position and the securement of the bracket cap 16 over the center channel 92.

FIG. 3 is a side sectional view taken along line 3-3 of FIG 1A depicting an exemplary embodiment of the self-ligating bracket 10 in the closed configuration. As depicted in FIGS. 1C, 2C, and 3, the arch wire slot 28 is defined by an occlusal wall 27, a gingival wall 29, and a bottom wall 31. In an exemplary embodiment, the arch wire slot 28 has a width of 0.022 inches for which coincides with a larger diameter of a standard rectangular arch wire; however, it will be recognized that other dimensions or configurations of the arch wire slot 28 may be used as disclosed in embodiments herein.

As described above, when the spring clip 14 is in the closed position, the respective distal arm 30, mesial arm 32, and center arm 34 bend at respective distal transition portion 40, mesial transition portion 46, and center transition portions 58 such that the distal finger 38, mesial finger 44, and center finger 54 is located into the arch wire slot at a position closer to the bottom 31 of the arch wire slot 28 than the rest of the spring clip 14. A distance D1 between the bottom of the respective fingers 38, 44, 54 of the spring clip 14 and the bottom 31 of the arch wire slot 28 defines a minimum diameter of arch wire required for active engagement of the arch wire by the spring clip 14. Thus, if an arch wire with a diameter smaller than D1 is used, the spring clip 14 will only actively engage the arch wire should the arch wire already be being forced out of seating in the arch wire slot 28, for example by a force labially away from the tooth.

Taking a hypothetical example where the wire is in alignment in the arch wire slot and seated at the bottom of the slot so that there are no corrective/interactive forces between the wire and the bracket, possible interactions between the clip and the wire will be explained. When an active self-ligating bracket is used with an arch wire with a smaller diameter than a distance (D1) between the bottom of the arch wire slot and the portion of the clip that extends into the slot, the active self-ligating bracket effectively operates as a passive bracket. However, when used with an arch wire of a diameter greater than the distance (D1) between the bottom of the arch wire slot and the clip, then clip engages the arch wire and applies the seating force. Thus, an active self-ligating bracket may be one in which a cross-sectional dimension of a lumen defined by the arch wire slot and the clip in the closed position is smaller than a cross-sectional dimension of at least one arch wire for which the arch wire slot is configured to receive.

A passive self-ligating bracket may be one in which a cross-sectional dimension of the lumen defined by the arch wire slot and the clip in the closed position is greater than a cross-sectional dimension of a largest arch wire for which the arch wire slot is configured to receive. The clip of the passive self-ligating bracket therefore does not engage any size of arch wire during treatment. Passive self-ligating brackets provide less control over bracket arch wire interaction, but do so with minimal friction (all else being equal) compared to elastomeric ligations and active clips which may improve transfer of the corrective force to the tooth. In some embodiments, the lumen of a passive self-ligating bracket may further be defined by a rigid ledge or other portion of the bracket body that engages the clip to define the minimum distance between the bottom of the arch wire slot and the clip in the closed position. The engagement of the clip with this structure of the bracket body may limit this minimum distance independent of the shape or other physical properties of the clip itself.

By way of example, a bracket may be designed for use with arch wires having a diameter in the facial-lingual dimension of 0.018 inch and with arch wires having a diameter in the facial-lingual dimension of 0.022 inch. In such an example, an active self-ligating bracket embodiment may be one with the aforementioned distance (D1) in the lumen is less than or equal to 0.022, while the clip in the closed position is capable of flexing to a distance (D1) of at least 0.022 inch while a passive self-ligating bracket is one in which the aforementioned distance (D1) in the lumen is greater than 0.022 inch, independent of the flexibility or rigidity of the clip.

Additionally, in an embodiment at least one of the end 39 of the distal arm 30, the end 45 of the mesial arm 32, and the end 55 of the center arm 54 engages the gingival wall 29 of the arch wire slot 28 when the spring clip is in the closed position and when the spring clip 14 is in the open position, the ends 39, 45, 55 are retracted into the bracket body occlusally of the occlusal wall 27 of the arch wire slot 28. In another embodiment, at least one of the end 39 of the distal arm 30, the end 45 of the mesial arm 32, and the end 55 of the center arm extend gingivally past a plane of the gingival wall 29, or end occlusally of the gingival wall 29. In either case, when the clip is in the open position, the respective ends 39, 45, 55 of the arms are retracted occlusally of the occlusal wall 27.

Some embodiments of the features described present additional advantages in that self-ligating bracket clips are typically tiny pieces of metal that if removed from engagement with the rest of the bracket, may become lost in a patient's mouth, swallowed by a patient, or cause abrasion to the inside of the patient's mouth. Therefore, a bracket that securely retains the spring clip when the clip is in the open position is beneficial. Additionally, retention of the spring clip in engagement with the rest of the bracket can minimize the risk of damage to the spring clip as the spring clip cannot be moved out of position.

FIGS. 7-11 depict a second exemplary embodiment of a self-ligating bracket 110. It will be recognized that in FIGS. 7-11 similar reference numerals as used and described above with respect to FIGS. 1-6 are further used herein to identify similar structures.

The self-ligating bracket 110 includes a bracket body 112 a spring clip 14 and a bonding pad 18. The bracket body 112 includes an arch wire slot 28 and tie wings 74. The arch wire slot 28 is defined by an occlusal wall 27, a gingival wall 29, and a bottom wall 31. The occlusal wall 27, gingival wall 29, and bottom wall 31 define a largest diameter or arch wire that can be accepted into the bracket 110.

Figure 9:
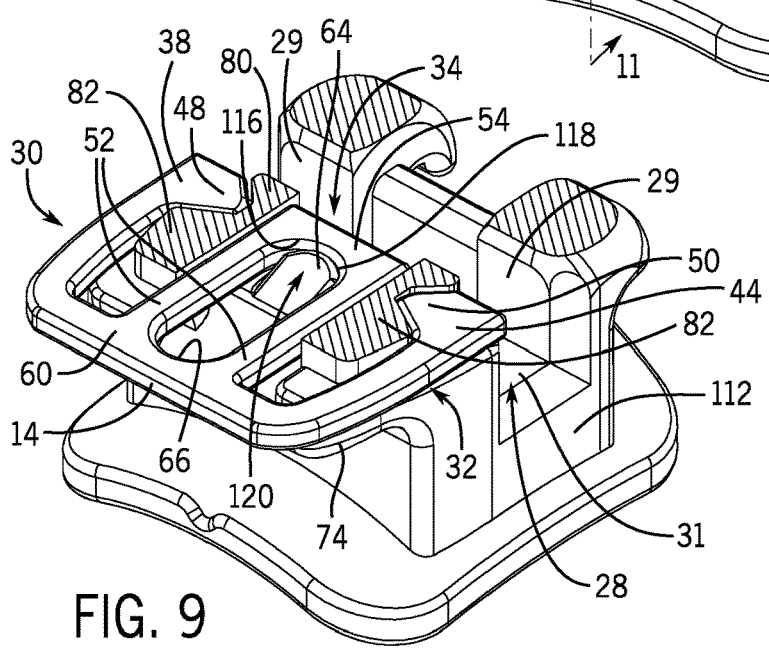
FIG. 9 is a cut away view of the second exemplary embodiment of the self-ligating bracket taken along the line 9-9 in FIG. 7.
Figure 10:
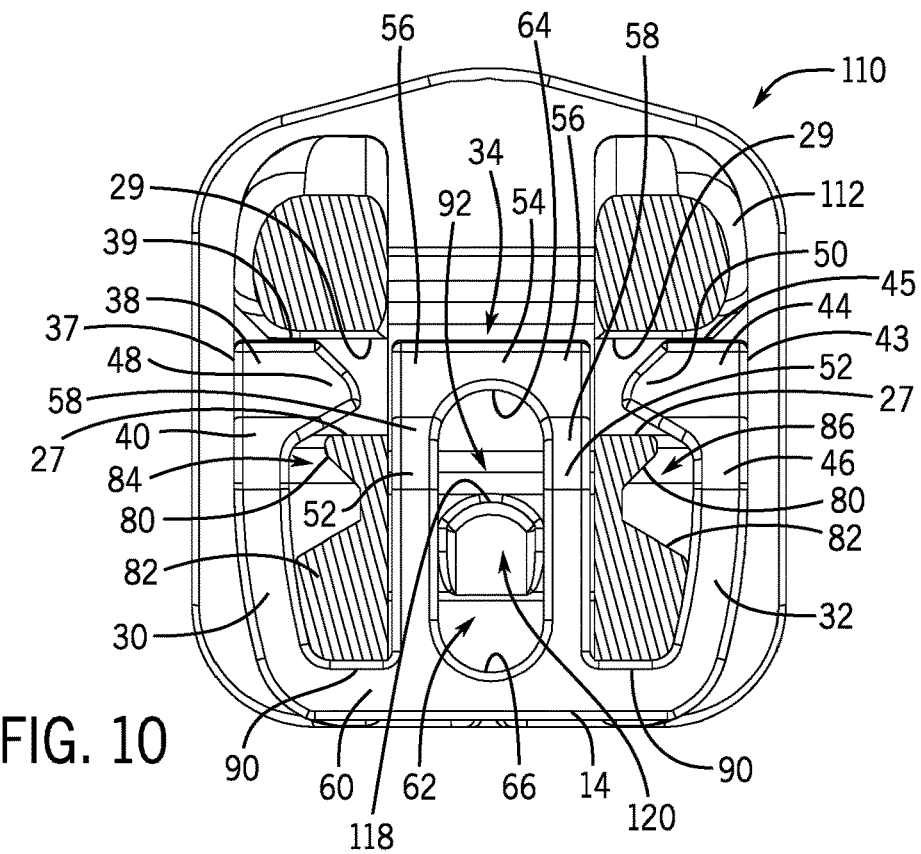
FIG. 10 is a top sectional view of the second exemplary embodiment of the self-ligating bracket as taken along line 10-10 of FIG. 8.

As best depicted in FIGS. 9 and 10, which are cut away views of self-ligating bracket 110, the bracket body 112 includes gingival stop projections 80 and occlusal stop projections 82. The gingival stop projections 80 and occlusal stop projections 82 respectively extend labially for at least the thickness of the spring clip 14 to define the distal channel 84 and mesial channel 86 in the labial dimension. The gingival stop projections 80 and occlusal stop projections 82 extend into the distal channel 84 within which the distal arm 30 of the spring clip 40 is slidingly received and the mesial channel 86 from which the mesial arm 32 of the spring clip 14 is slidably received. The bracket body 112 further includes a center channel 92 within which the center arm 34 of the spring clip 14 slidingly moves.

As previously described, the center arm 34 includes center arm bars 52 which terminate at an end bar 54 connecting gingival ends 56 of respective center arm bars 52. The spring clip further defines a center opening 62 bounded by the center arm bars 52, end bar 54 and base bar 60 of the spring clip 14. The center opening 62 is exemplarily defined between a first end 64 and a second end 66. As will be described in further detail herein, the first end 64 and second end 66 of the center opening 62 are exemplarily curved shaped. It will be recognized, however, that other shapes of the first end 64 and second end 66 may be used in this embodiment and in other embodiments while remaining within the scope of the present disclosure.

The distal arm 30 includes a distal transition portion 40, the mesial arm 32 includes a mesial transition portion 46, and the center arm 34 includes center transition portions 58. Each of the transition portions 40, 46, and 58 are exemplarily shaped as S-curves while other configurations will be recognized from the present disclosure.

Referring back to FIGS. 7 and 8, the bracket body 112 includes tie wing caps 114 that are integral components of the bracket body 112. The tie wing caps 114 exemplarily extend from the gingival stop projections 80 and the occlusal stop projections 82 and cover above the respective distal channel 84 and mesial channel 86, while leaving the center channel 92 exemplarily exposed.

The bracket body 112 further includes a stop projection 116 that extends from a channel floor 96 of the center channel 92. The stop projection 116 further includes a gingival shoulder 118 and an occlusal ramp 120.

In operation, the self-ligating bracket 110 is assembled by inserting the spring clip 14 into the occlusal side of the bracket body 112 and slide the distal arm 30 and mesial arm 32 within the respective distal channel 84 and mesial channel 86 of the bracket body 112. As the spring clip 14 is inserted, the distal arm 30 and mesial arm 32 deform in the mesial-distal dimension so that the respective distal projection 48 and mesial projection 50 can pass around first the occlusal stop projection 82 and later the gingival stop projection 80, when the spring clip is moved into the closed position.

As the spring clip 14 is advanced in the gingival direction, the end bar 54 engages the occlusal ramp 120 of the stop projection 116. The occlusal ramp 120 deforms the center arm 34 outward in an exemplary facial direction until the first end 64 of the center opening 62 passes over the gingival shoulder 118 of the stop projection 116.

As mentioned above, if the spring clip 14 advances further in the exemplary gingival direction, the respective transition portions 40, 58, and 46 of the spring clip arms pass over the shoulders 98 and the distal finger 38, end bar 54, and mesial finger 44 extend into and across the arch wire slot 28 as the transition portions 40, 46, and 58 return to their normal position. In this position, the distal finger end 39 and mesial finger end 45 engage the gingival wall 29 of the arch wire slot 28.

Figure 7:
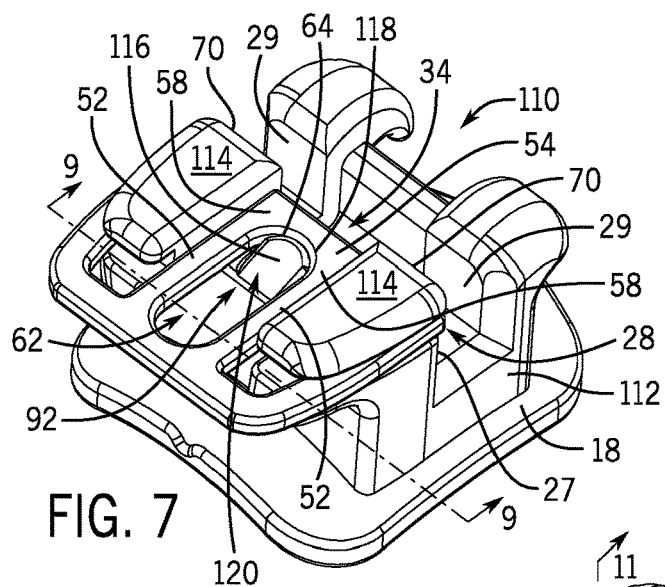
FIG. 7 depicts a perspective view of a second exemplary embodiment of a self-ligating bracket in an open configuration.
Figure 8:
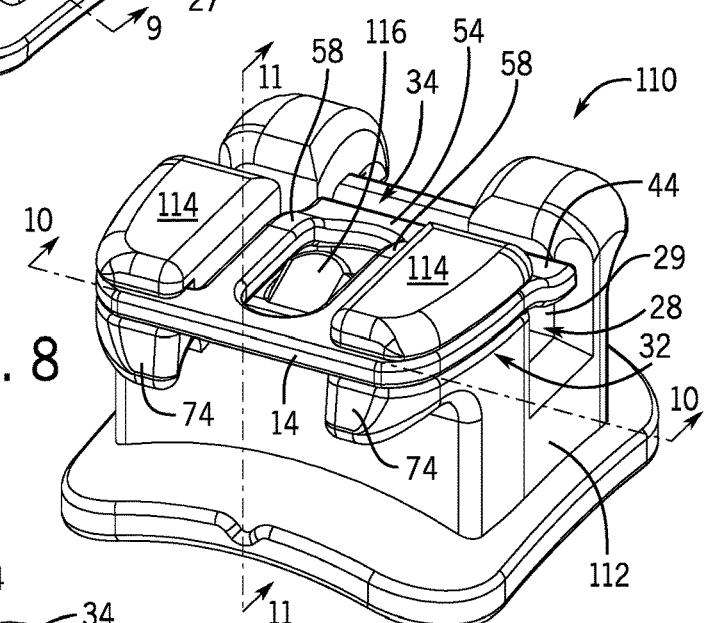
FIG. 8 depicts a perspective view of the second exemplary embodiment of the self-ligating bracket in a closed configuration.
Figure 11:
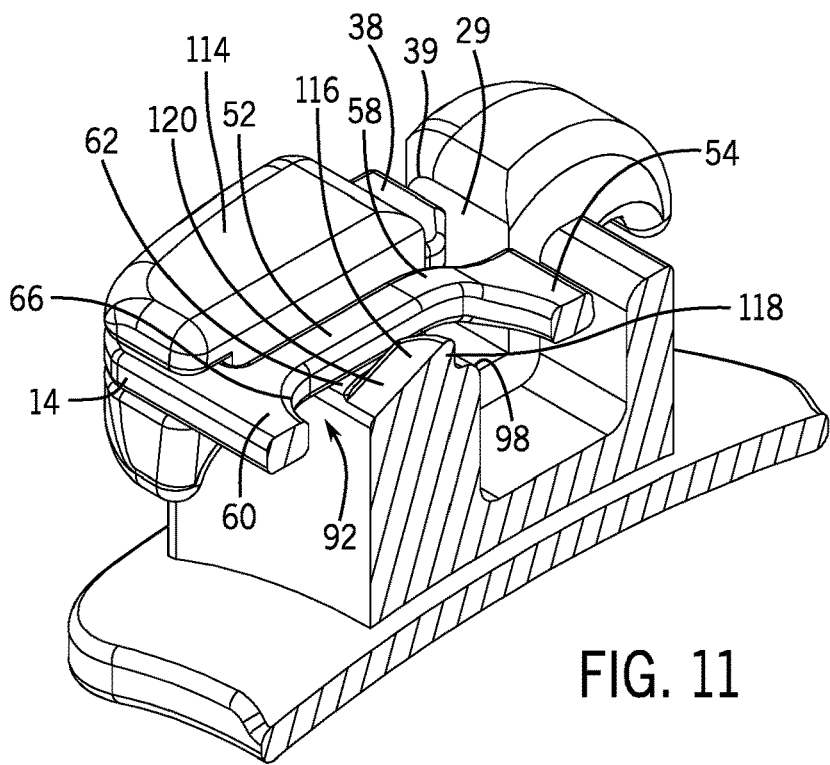
FIG. 11 is a perspective sectional view taken along line 11-11 of FIG. 8.

As best depicted in FIGS. 7, 9, and 11, when the spring clip 14 is moved from the closed position to the open position, the distal arm 30 and mesial arm 32 operate in the same manner as described above with respect to FIGS. 1-6. The center arm 34 operates in an alternative manner as the center arm 34 is not retained in engagement with the bracket body 112 by the bracket cap 16 as in the first embodiment (FIGS. 1-6). Rather, as the transition portions 58 of the center arm 34 are deformed to move past the shoulder 98 from the closed position to the open position, an inward or exemplarily lingual force is placed on the end bar 54 in conjunction with the engagement of the gingival shoulder 118 against the first end 64 of the center opening 62. These two engagements combine to prevent the end bar 54 from being able to move past the gingival shoulder 118 of the stop projection 116. The engagement of the gingival shoulder 1189 of the stop projection 116 with the first end 64 of the center opening 62 prevents further occlusal movement of the clip 14. The force of the transition portions 58 pressing the end bar 55 against the top of shoulder 98 and/or the channel floor 96 gingival of the stop projection 92 keeps the center bar 54 from moving facially to move over the stop projection 92. As such, when the spring clip 14 is in the open position as exemplarily depicted in FIGS. 7 and 9, the spring clip 14 is held from any further movement in the exemplary occlusal direction as such movement would require additional deforming forces both against the end bar 54 in the facial direction to move past the stop projection 116 and against the distal arm 30 and mesial arm 32 outwardly in the mesial-distal dimension to respectively move the distal projection 48 and mesial projection 50 out of respective engagement with the occlusal stop projections 82. As such combination of forces cannot be practically applied to the spring clip in the open position, the spring clip 14 is effectively locked into engagement with the bracket body 112 and is not removable without damaging one or more components of the self-ligating bracket 110.

The self-ligating bracket as described herein present advantages over current self-ligating bracket solutions by providing a clip that is moveably secured to the bracket body in a manner that prevents its removal.

Self-ligating brackets as described herein may further provide improved active ligation by separately engaging an arch wire positioned in the arch wire slot at at least two, and in some embodiments three, locations: the distal end of the slot, the mesial end of the slot, and at the center of the slot. During use, the arch wire necessarily experiences uneven interaction with the arch wire slot and the clip. This imbalance in interactions direct the tooth to the desired corrected position. Only after the tooth is in the corrected position (as can be achieved with a particular arch wire dimension) and can freely move within the arch wire slot. Therefore, the spring clips as disclosed herein are able to individually provide active force against the arch wire with each slot when torque on the tooth/bracket causes the arch wire to unevenly interact with the clip. The separate arms engage the wire independently and therefore maintain engagement by each arm during treatment.

Self-ligating brackets as described herein provide the above-mentioned at least two and in some embodiments, three independent areas of active force, but also, with the center bar, and distal and mesial projections of the distal and mesial fingers, engage the arch wire across a substantial width of the total arch wire slot width. Embodiments as disclosed herein may engage the arch wire across greater than 60%, 80%, 85%, or greater than 90% of the arch wire slot width. Thus, while the brackets disclosed herein may provide three independent areas of active ligating force, such forces are also applied across a substantial portion of the width of the arch wire slot and bracket. The distal projections and mesial projections serve multiple functions of retaining the spring clip in the open position (by engagement with the gingival projections), retaining the spring clip to the bracket body (by engagement with the occlusal projections), and increasing the area of engagement with the arch wire.

While the present disclosure uses the specific example of a bracket such as one configured for use on an incisor or canine, it will be recognized that as used herein, self-ligating brackets may similarly exemplarily refer to buccal tubes, convertible orthodontic appliances, and/or other orthodontic appliances which may include a self-ligating clip as described herein.

Certain relative directional terms including, but not limited to occlusal, gingival, mesial, distal, buccal, labial, lingual, facial have been used within the present description in reference to a particular exemplary orientation on a patient's body. It will be recognized that these are merely exemplary and that a bracket having the same features may be oriented differently on any particular patient.

This written description uses examples to disclose the invention, including the best mode, and also to enable any person skilled in the art to make and use the invention. It will be recognized that features described herein with respect to one embodiment may be combined with features disclosed with respect to other embodiments herein while remaining within the scope of the disclosed invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A self-ligating bracket comprising:
   a bracket body having a mesial side and a distal side, the bracket body comprising an arch wire slot that extends from the mesial side to the distal side of the bracket body, a mesial channel that extends into the bracket body, a distal channel that extends into the bracket body, and a center channel extending into the bracket body between the mesial channel and the distal channel; and
   a spring clip comprising a distal arm comprising a distal arm body and a distal finger, a mesial arm comprising a mesial arm body and a mesial finger, and a center arm comprising a first center arm body and a second center arm body connected by a center arm bar; and
   wherein the spring clip is movable with the distal arm in the distal channel, the mesial arm in the mesial channel, and the center arm in the center channel, between an open position and a closed position wherein in the open position, the arch wire slot is unobstructed and in the closed position, the distal finger, the mesial finger and the center arm bar extend into and across the arch wire slot to occlude the arch wire slot with the distal finger, the mesial finger, and the center arm bar.

2. The self-ligating bracket of claim 1, further comprising:
   at least one bracket cap secured over the bracket body and defining a labial side of the distal channel and a labial side of the mesial channel.

3. The self-ligating bracket of claim 2, wherein the at least one bracket cap comprises a distal bracket cap integrally formed with the bracket body and defining the labial side of the distal channel and a mesial bracket cap integrally formed with the bracket body and defining the labial side of the mesial channel.

4. The self-ligating bracket of claim 2, wherein the at least one bracket cap is a single bracket cap secured to the bracket body across the distal channel, center channel, and mesial channel, the single bracket cap defining a labial side of the center channel.

5. The self-ligating bracket of claim 1, wherein a combined width in a mesial-distal dimension of the distal finger, mesial finger, and center arm bar is at least 60% of a width of the arch wire slot in the mesial-distal dimension.

6. The self-ligating bracket of claim 1, wherein the distal finger comprises a distal projection that extends in a mesial direction and the mesial finger comprises a mesial projection that extends in a distal direction.

7. The self-ligating bracket of claim 6, wherein the bracket body further comprises:
   a first gingival projection that extends distally within the distal channel;
   a second gingival projection that extends mesially within the mesial channel;
   a first occlusal projection that extends distally within the distal channel; and
   a second occlusal projection that extends mesially within the mesial channel;
   wherein the distal projection of the distal arm engages the first gingival projection and the first occlusal projection and the mesial projection of the mesial arm engages the second gingival projection and the second occlusal projection to restrain the spring clip in the open position.

8. The self-ligating bracket of claim 6, wherein a combined width in a mesial-distal dimension of the distal finger, mesial finger, and center arm bar is at least 85% of a width of the arch wire slot in the mesial-distal dimension.

9. The self-ligating bracket of claim 1, wherein when the spring clip is in the closed position, the distal finger, the mesial finger, and the center arm bar extend into the arch wire slot to a position such that a distance between the distal finger, mesial finger, and the center arm bar and a bottom wall of the arch wire slot is smaller than a similar dimension of at least one arch wire configured to be received in the arch wire slot.

10. The self-ligating bracket of claim 1, wherein the spring clip further comprises:
    a distal transition portion between the distal arm body and the distal finger;
    a mesial transition portion between the mesial arm body and the mesial finger;
    a first center transition portion between the first center arm body and the center arm bar; and
    a second center transition portion between the second center arm body and the center arm bar;
    wherein the distal arm body, mesial arm body, first center arm body, and second center arm body are all co-planar in a first plane and the distal finger, mesial finger and the center arm bar are all co-planar in a second plane and the first plane is different from the second plane.

11. The self-ligating bracket of claim 10, further comprising:
    a distal shoulder between the distal channel and the arch wire slot;
    a mesial shoulder between the mesial channel and the arch wire slot; and
    a center shoulder between the center channel and the arch wire slot; and
    wherein when the spring clip is in the closed position, the distal transition portion resiliently engages the distal shoulder, the mesial transition portion resiliently engages the mesial shoulder and the first and second center transition portions resiliently engage the center shoulder to bias the spring clip in the closed position.

12. The self-ligating bracket of claim 1, wherein the bracket body comprises a distal tie wing on the distal side and a mesial tie wing on the mesial side, the distal channel extends into the distal tie wing from the distal side of the bracket body, the mesial channel extends into the mesial tie wing from the mesial side of the body, and the center channel extends into the bracket body between the distal tie wing and the mesial tie wing.

\* \* \* \* \*